(12) United States Patent
Livneh (10) Patent No.: US 9,895,187 B2
(45) Date of Patent: Feb. 20, 2018

(54) SCANNING CANNULA (75) Inventor: Steve Livneh, Amherstburg (CA)

(73) Assignee: RF KINETICS INC., Amherstburg, Ontario (CA)

( * ) Notice: Subject to any disclaimer, the term of this patent is extended or adjusted under 35 U.S.C. 154(b) by 816 days.

(21) Appl. No.: 13/127,577

(22) PCT Filed: Nov. 12, 2009

(86) PCT No.: PCT/US2009/064185
§ 371 (c)(1),
(2), (4) Date: May 4, 2011

(87) PCT Pub. No.: WO2010/059501
PCT Pub. Date: May 27, 2010

(65) Prior Publication Data
US 2011/0221463 A1 Sep. 15, 2011

Related U.S. Application Data (60) Provisional application No. 61/116,395, filed on Nov. 20, 2008.

(51) Int. Cl.
*A61B 18/12* (2006.01)
*A61B 18/00* (2006.01)
(Continued)

(52) U.S. Cl.
CPC ...... *A61B 18/1233* (2013.01); *A61B 17/3462* (2013.01); *A61B 18/1482* (2013.01);
(Continued)

(58) Field of Classification Search
CPC ..... G01R 31/00–31/20; A61B 17/3462; A61B 18/14; A61B 18/18; A61B 6/586;
(Continued)

(56) References Cited

U.S. PATENT DOCUMENTS 3,614,605 A * 10/1971 Eisele .......................... 324/557
4,477,769 A * 10/1984 Lowery et al. ............... 324/517
(Continued)

FOREIGN PATENT DOCUMENTS

| CN | 1260062 | 7/2000 |
|---|---|---|
| EP | 3 002 595 A1 | 4/2016 |
| WO | 98/45822 | 10/1998 |

OTHER PUBLICATIONS

Office Action dated Mar. 5, 2013 in Chinese application No. 200980146205.8 and English translation.
Extended Search Report dated Jul. 7, 2016.

*Primary Examiner* — Joseph Stoklosa
*Assistant Examiner* — Eunhwa Kim
(74) *Attorney, Agent, or Firm* — Howard & Howard Attorneys PLLC (57) ABSTRACT

A scanning cannula for scanning an electrosurgical instrument for electrical insulation defects includes an elongated sleeve having a receiving end, an opposite exit end, and a passageway extending from the receiving end to the exit end. At least one sweeping contact is disposed in the passageway. A circuit in the sleeve is electrically connected to the at least one sweeping contact. A communication device is connected to the circuit to transmit signals from the circuit to a switchbox of a surgical instrument. An electrosurgical instrument inserted into the receiving end of the sleeve passes through the at least one sweeping contact, and any electrical defect of the electrosurgical instrument detected by the at least one sweeping contact is relayed as an error signal to the circuit, which communicates the error signal to the switchbox. The switchbox cuts current to the electrosurgical instrument and signals an alarm.

20 Claims, 6 Drawing Sheets

(51) Int. Cl.
*A61B 18/14* (2006.01)
*A61B 17/34* (2006.01)

(52) U.S. Cl.
CPC ............ *A61B 2018/00083* (2013.01); *A61B 2018/00178* (2013.01); *A61B 2018/00708* (2013.01); *A61B 2018/00827* (2013.01); *A61B 2018/00898* (2013.01)

(58) Field of Classification Search
CPC ........... A61B 1/00057; A61B 18/1233; A61B 2018/00678; A61B 2018/1226; A61B 2018/00827; A61B 2018/007
USPC ........... 606/34; 324/557–559, 541, 551, 71.1
See application file for complete search history.

(56) References Cited

U.S. PATENT DOCUMENTS

| | | |
|---|---|---|
| 4,644,610 A | 2/1987 | Fish |
| 4,857,857 A | 8/1989 | Valenti |
| 5,312,327 A | 5/1994 | Bales et al. |
| 5,552,713 A | 9/1996 | Rashidi |
| 5,676,678 A | 10/1997 | Schad |
| 5,688,269 A * | 11/1997 | Newton ............. A61B 18/1233 606/35 |
| 5,908,402 A * | 6/1999 | Blythe ............................ 604/26 |
| 5,936,536 A | 8/1999 | Morris |
| 6,039,734 A | 3/2000 | Goble |
| 6,042,573 A * | 3/2000 | Lucey ................ A61B 17/3423 604/23 |
| 6,077,290 A | 6/2000 | Marini |
| 6,376,766 B1 | 4/2002 | Bartholoma et al. |
| 6,494,880 B1 | 12/2002 | Swanson et al. |
| 6,977,509 B2 * | 12/2005 | Carroll et al. ................ 324/544 |
| 7,018,331 B2 | 3/2006 | Chang et al. |
| 2002/0188173 A1 * | 12/2002 | Kobayashi ..................... 600/118 |
| 2007/0179489 A1 | 8/2007 | Dodde et al. |
| 2011/0221463 A1 | 9/2011 | Livneh |
| 2014/0100478 A1 | 4/2014 | Speeg |

\* cited by examiner

SCANNING CANNULA

TECHNICAL FIELD

This invention relates to electrosurgery, and more particularly to cannulas for use in electrosurgery.

BACKGROUND OF THE INVENTION

Electrosurgery (ES) and specifically endoscopic ES (EES) are fast growing technologies that expanded a surgeon's capabilities to cut, coagulate, and cauterize tissue and vessels with unprecedented efficiency.

However, ES involves the application of high voltage to the working elements of an ES device. Thus, the danger of undesired electrocution and even severe burns always exists and great efforts have been devoted towards implementing durable insulation and protective means, to protect both the surgeon and the patient.

SUMMARY OF THE INVENTION

The present invention provides a scanning cannula for automatic scanning of endoscopic ES devices. The scanning cannula has scanning capabilities for detecting arcing and leakage currents through the ES device when the ES device is inserted through the cannula. The present invention thereby adds an active safety measure to electrosurgery, specifically the checking of all devices upon insertion through the scanning cannula.

The present invention provides a stand-alone scanning cannula that scans mostly tubular insulated elements, typically the working shafts of RF electrosurgical monopolar and hybrid instruments (i.e., RF devices capable of mono-bipolar energy modes), for insulation imperfections and leakage current by communicating via wires or wirelessly with a wired or wirelessly controlled switchbox or an RF generator having added circuitry necessary to eliminate the switchbox.

The scanning cannula, in its wireless form, according to the present invention eliminates unnecessary wires which are normally required for the operation of conventional devices used in electrosurgery. The scanning cannula further includes control mechanisms related to the scan cycle. The scanning cannula also may have illumination and insufflation pressure monitoring and even regulating capabilities, thus making it far more valuable than an inert access device.

A scanning cannula in accordance with the present invention that scans an electrosurgical instrument for electrical defects includes an elongated sleeve having a receiving end, an opposite exit end, and a passageway extending from the receiving end to the exit end. At least one sweeping contact is disposed in the passageway. A circuit in the sleeve is electrically connected to the at least one sweeping contact. A communication device is connected to the circuit to transmit signals from the circuit to a switchbox of a surgical instrument. An electrosurgical instrument inserted into the receiving end of the sleeve passes through the at least one sweeping contact, and any electrical defect of the electrosurgical instrument detected by the at least one sweeping contact is relayed as an error signal to the circuit, which communicates the error signal to the switchbox.

Optionally, each sweeping contact may be a disk-shaped ring including a plurality of fingers extending towards a hollow center of the ring. The sweeping cannula may include a pair of sweeping contacts spacedly disposed from each other in the passageway. The communication device may include an antenna that wirelessly transmits signals to the switchbox. Alternatively, the communication device may include a cable that electrically transmits signals to the switchbox. The circuit may include a battery that powers the scanning cannula. The circuit may include a capacitor electrically connected to each of the at least one sweeping contact. The circuit may include two or more LEDs that display status information.

The scanning cannula may include a photo cell disposed in the passageway downstream of the at least one sweeping contact. The photo cell may be electrically connected to the circuit, and the photo cell may detect the presence of an electrosurgical instrument in the passageway. The scanning cannula may include a light source in communication with an optical fiber disposed along a length of the sleeve to illuminate the sleeve and the internal surroundings. The scanning cannula may include a pressure sensor electrically connected to the circuit, and a conduit in fluid communication with the pressure sensor for dynamic monitoring of insufflation pressure.

A method of scanning an electrosurgical instrument for electrical defects in accordance with the present invention includes the steps of providing an elongated sleeve having a receiving end, an opposite exit end, and a passageway extending from the receiving end to the exit end; disposing at least one sweeping contact in the passageway; mounting a circuit in the sleeve; electrically connecting the at least one sweeping contact to the circuit; connecting a communication device to the circuit to transmit signals from the circuit to a switchbox of a surgical instrument; inserting an electrosurgical instrument into the receiving end of the sleeve; passing the electrosurgical instrument through the at least one sweeping contact, whereby any electrical defect of the electrosurgical instrument detected by the at least one sweeping contact is relayed as an error signal to the circuit; and communicating the error signal to the switchbox.

Optionally, the communication device may include an antenna, and the error signal may be wirelessly communicated from the circuit to the switchbox. Alternatively, the communication device may include a cable that is electrically connected to the circuit and the switchbox, and the error signal may be communicated from the circuit to the switchbox through the cable. When the error signal is communicated from the circuit to the switchbox, the switchbox may perform one or more of the following: displaying a warning signal, and cutting power to the electrosurgical device.

An electrosurgical system in accordance with the present invention for scanning an electrosurgical instrument for electrical defects includes a scanning cannula including: an elongated sleeve having a receiving end, an opposite exit end, and a passageway extending from the receiving end to the exit end; at least one sweeping contact disposed in the passageway; a circuit mounted in the sleeve, the at least one sweeping contact being electrically connected to the circuit; and a communication device connected to the circuit to transmit signals from the circuit. A switchbox is in communication with the scanning cannula. An electrosurgical generator is electrically connected to the switchbox. An electrosurgical instrument is electrically connected to the switchbox. The electrosurgical instrument is inserted into the receiving end of the sleeve and passes through the at least one sweeping contact. Any electrical defect of the electrosurgical instrument detected by the at least one sweeping contact is relayed as an error signal to the circuit, which communicates the error signal to the switchbox.

Optionally, the communication device may include an antenna, and the circuit may wirelessly communicate with the switchbox via the antenna. Alternatively, the communication device may include a cable that is electrically connected to the circuit and the switchbox, and the circuit may communicate with the switchbox through the cable. Upon receiving an error signal from the scanning cannula, the switchbox may perform one or more of the following: displaying a warning signal, and cutting power to the electrosurgical device.

These and other features and advantages of the invention will be more fully understood from the following detailed description of the invention taken together with the accompanying drawings.

DETAILED DESCRIPTION OF THE INVENTION

Referring now to the drawings in detail, numeral 10 generally indicates a scanning cannula in accordance with the invention. The scanning cannula 10 provides for scanning of an electrosurgical instrument and detection of electrical malfunctioning of the instrument, which increases the safety of the instrument and related electrosurgical procedures.

Figure 1:
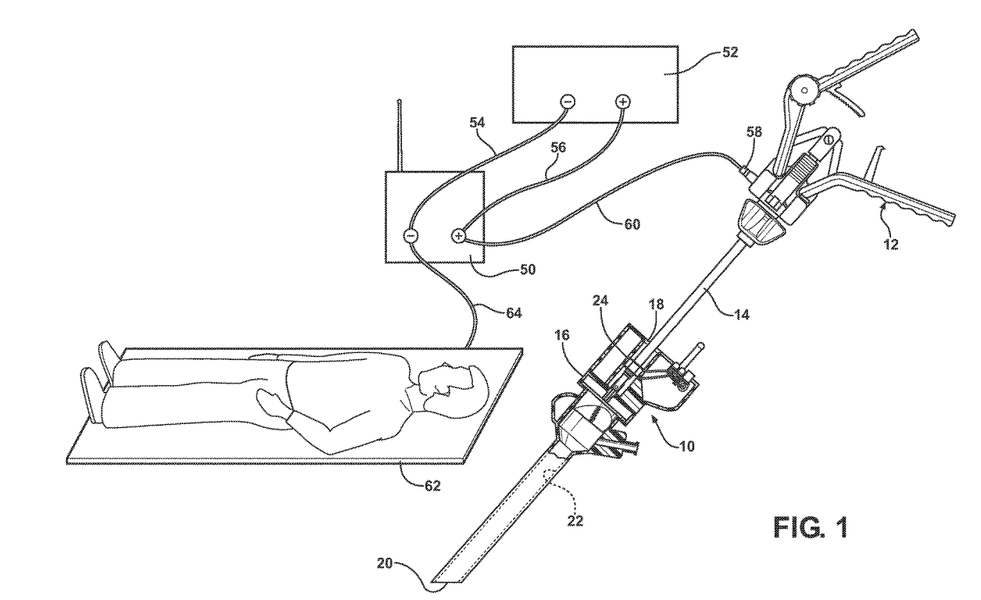
FIG. 1 is an environmental view of a wireless scanning cannula in accordance with the invention having an electrosurgical instrument inserted therein.
Figure 2:
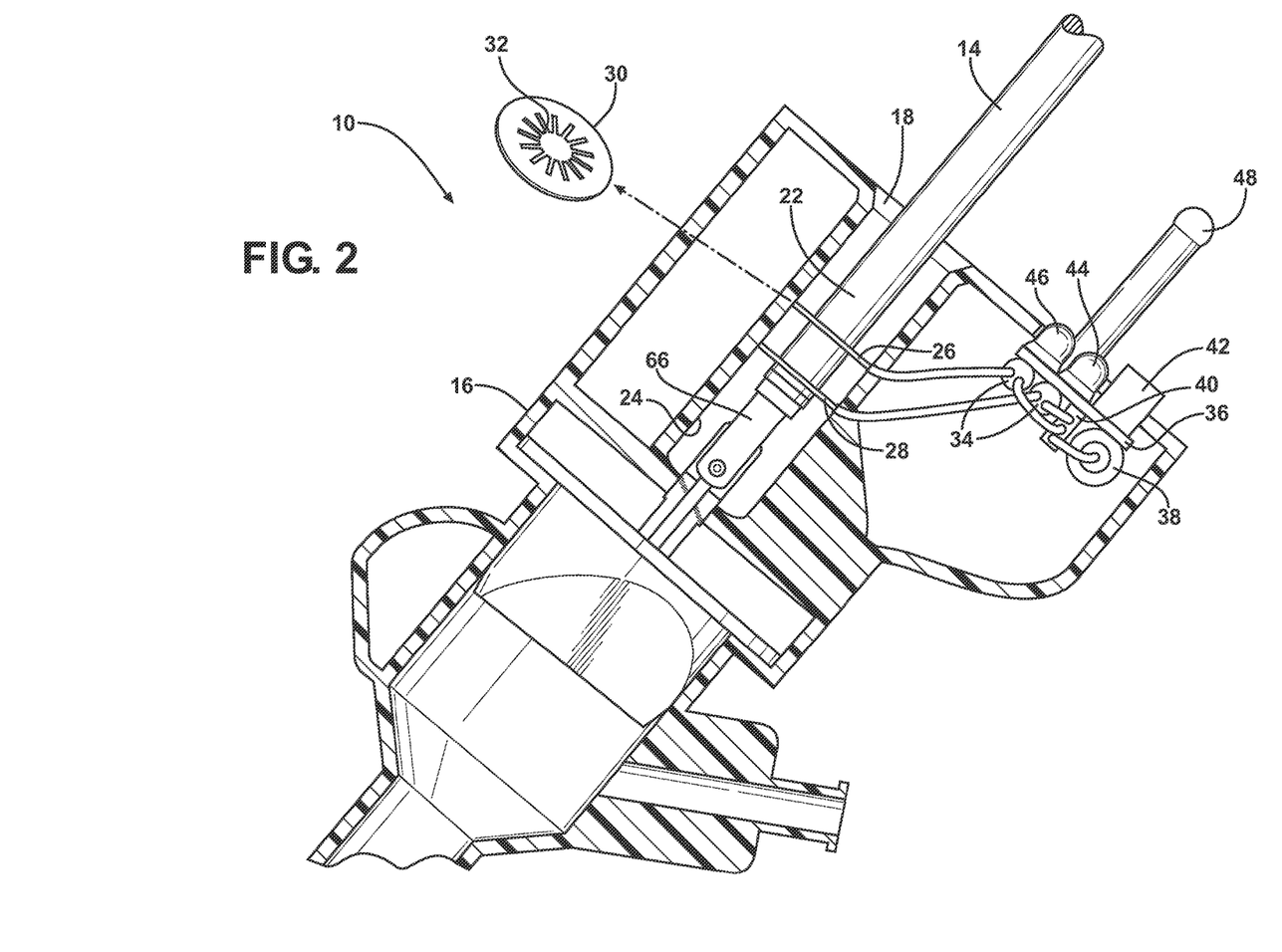
FIG. 2 is an enlarged view of a portion of the wireless scanning cannula.
Figure 3:
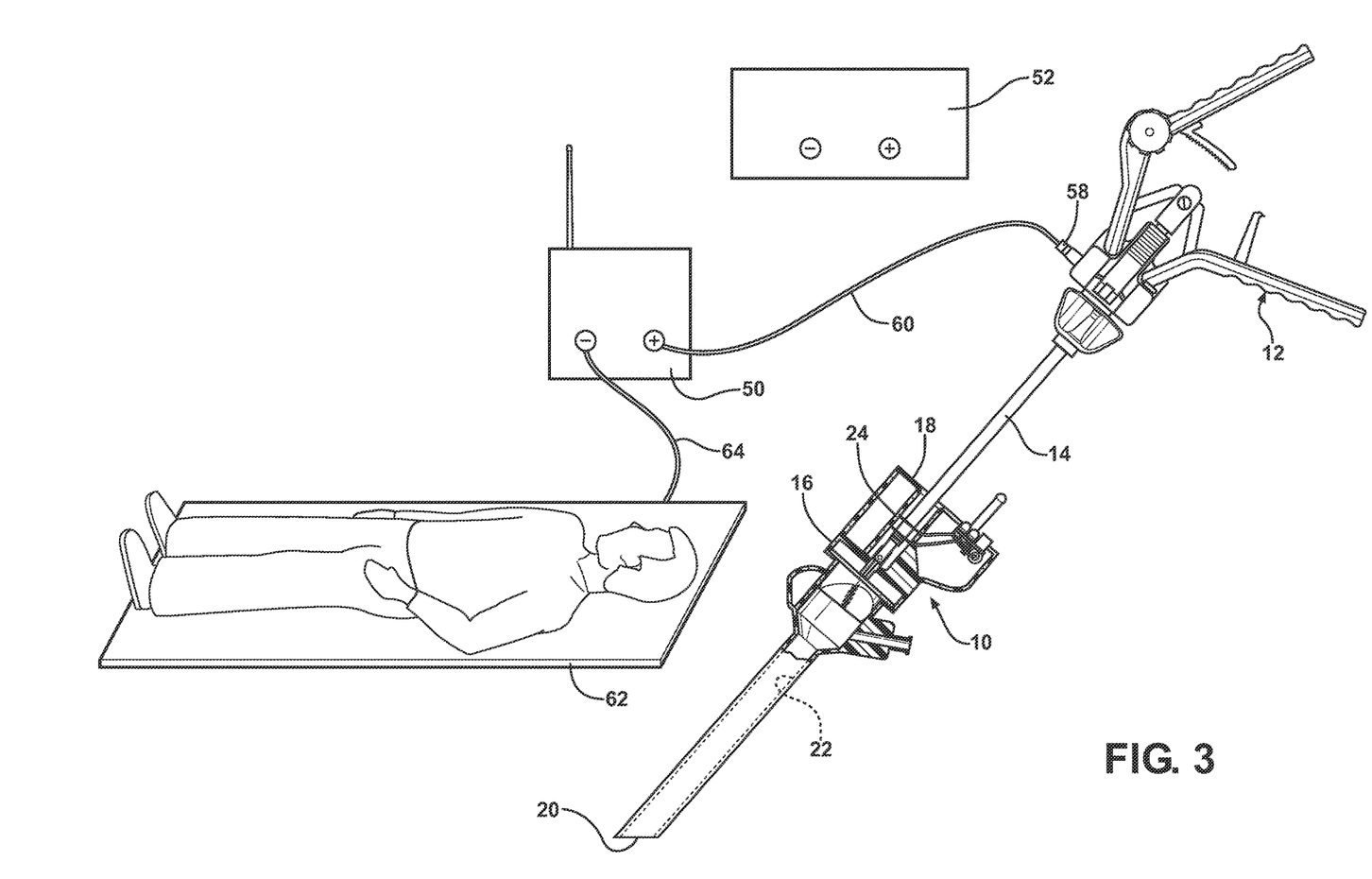
FIG. 3 is an environmental view of the wireless scanning cannula and its related circuit in scanning mode.

As illustrated in FIGS. 1 through 3, an endoscopic, monopolar (RF) surgical device 12 such as an electrosurgical instrument having an insulated shaft 14 is partially inserted into the scanning cannula 10. The insulated shaft 14 of the surgical device 12 is scanned for insulation defects by the scanning cannula 10 as described herein.

The scanning cannula 10 includes an elongated sleeve 16 having an instrument receiving end 18, an opposite exit end 20, and a passageway 22 extending from the receiving end to the exit end. A portion of the passageway 22 adjacent the receiving end 18 defines a scanning chamber 24. Two sweeping contacts 26, 28 are disposed in the scanning chamber 24 and are spaced apart at a safe distance to avoid arcing (e.g., between 1 mm and 8 mm). Each sweeping contact 26, 28 may be a disk-shaped ring 30 including a plurality of fingers 32 extending towards a hollow center of the ring. A circuit such as a printed circuit board (PCB) 36 or similar circuit arrangement is mounted in or on or integral with the sleeve 16. The sweeping contacts 26, 28 are each separately wired to a capacitor 34 included in the PCB 36. The PCB 36 includes a battery 38, the two capacitors 34 each electrically connected to a separate sweeping contact 26, 28, a voltage buildup mechanism 40 between the battery 38 and capacitors 34, a control mechanism (activation button 42 such as an on/off switch or similar), two LEDs 44, 46 (although more than two LEDs may be included), and a communication device 48 to transmit signals from the PCB 36. In one embodiment, the communication device 48 may include an antenna that wirelessly transmits necessary signals from the PCB 36 to a wireless switchbox 50 that is electrically connected to the surgical device 12.

FIG. 1 illustrates "normal" wiring as to be used in surgery. The wirelessly controlled switchbox 50 is connected to monopolar and ground ports on an electrosurgical generator 52 via cables 54, 56. The surgical device 12 is wired to the monopolar port on the switchbox 50 via a power plug 58 and cable 60. A ground pad 62, which is attached to a patient, is connected to the switchbox 50 ground via a cable 64.

FIG. 2 illustrates a typical situation pertaining to a scanning function of the scanning cannula 10. In a scanning mode, activation button 42 is depressed (switched to the on position), and the battery 38 charges the capacitors 34 and sweeping contacts 26, 28 with high voltage. At the same time, antenna 48 transmits a signal to the switchbox 50 to switch the circuits as shown in FIG. 3. When the capacitors 34 are charged, green LED 46 indicates that the scanning cannula 10 is ready for a scanning procedure.

A practitioner such as a surgeon or other health care provider inserts the shaft 14 of the surgical device 12 into the scanning chamber 24 through the receiving end 18 of sleeve 16. The scanning then proceeds as follows. Exposed jaw assembly 66, at a distal end of the insulated shaft 14, is inserted through a tubular inlet (at receiving end 18) of the scanning chamber 24 and moved through the charged sweeping contacts 26, 28. The initial passage of the exposed jaw assembly portion 66 is detected by arcing from sweeping contacts 26, 28 onto the exposed jaw portion 66. The arcing may be controlled by a circuit designed to reduce current flow upon arcing. The residual current flows either through the tubular conductive conductor in the shaft 14 or an internal conductive activation shaft into the power-plug 58, through cable 60 into the switchbox 50, and from the switchbox 50 to the patient ground pad 62 via cable 64. Another ground reference may be achieved by having the switchbox include an attached ground wire, thus avoiding the use of patient capacitance as the ground reference (see FIG. 6). The moment at which both sweeping contacts 26, 28 cease to arc is considered to be the beginning of the scan. Any further arcing from sweeping contact 26 is identified as a defect in insulation. The data is processed by the PCB 36 and transmitted to switchbox 50. The signal leads to a warning on either or both of the scanning cannula 10 and the switchbox 50, and eventually to the cutting of power from the generator 52 to the surgical device 12 upon completion of the scanning. The scan itself, if executed automatically, is limited in time to 15 seconds, for example. After the scan, if no arcing was detected during the scan period, an OK signal appears on both the scanning cannula 10 and the switchbox 50. The scan duration and scan initiation may be controlled manually by switching the switchbox 50 to scan mode and switching the switchbox 50 back to normal work mode once the surgical device 12 has been inserted and no alarm was displayed.

Figure 4:
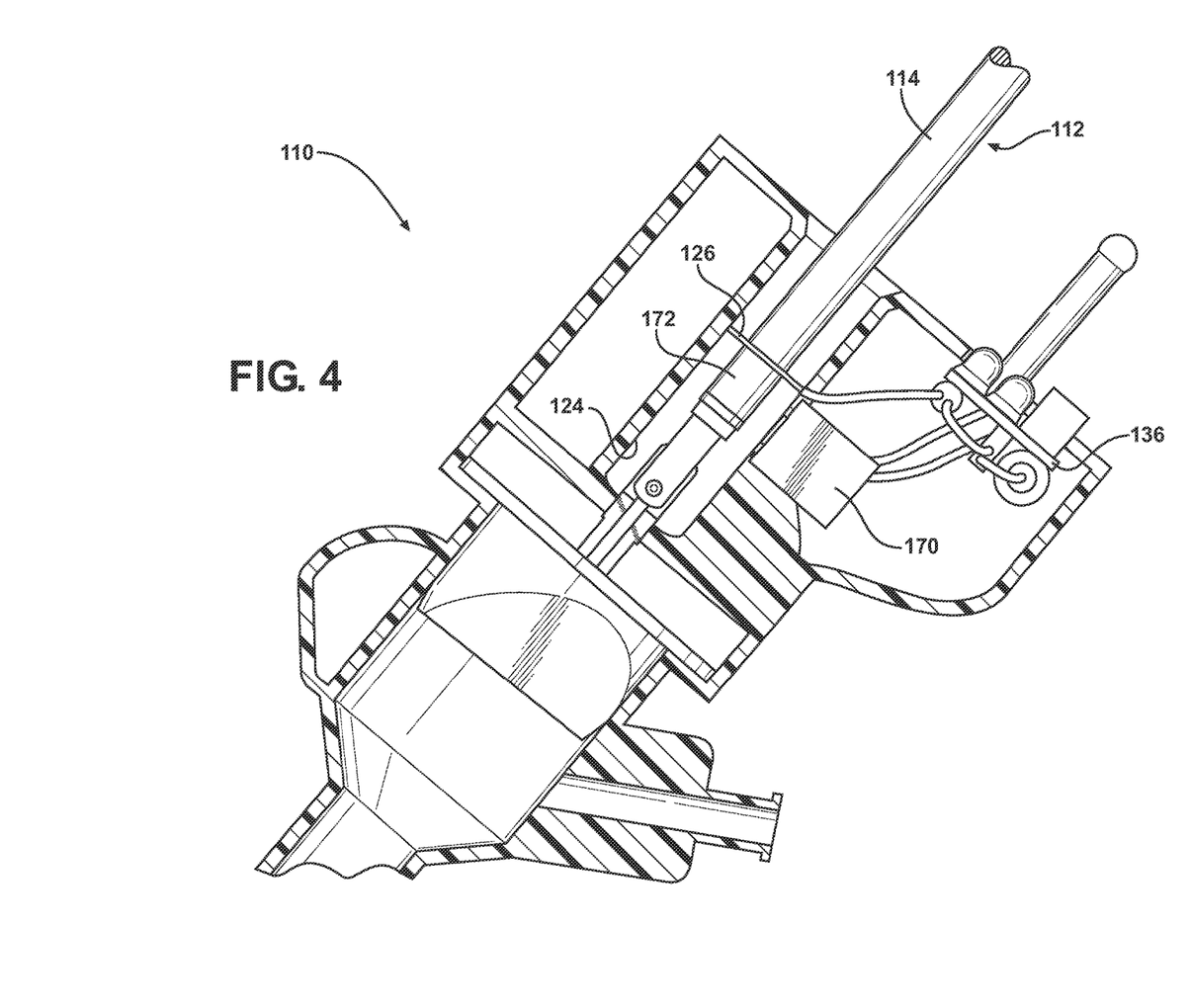
FIG. 4 is a partial view of an alternative embodiment of a scanning cannula in accordance with the invention.

FIG. 4 illustrates another embodiment of detection at the beginning of the scanning procedure. In this embodiment, the scanning cannula 110 includes one sweeping contact 126. A photo or light cell 170 is disposed below (downstream of) the single sweeping contact 126 in the scanning chamber 124. The photo cell 170 is electrically connected to the PCB 136. The photo cell 170 may detect the presence of the dark insulating sheath 172 of the shaft 114, indicating the PCB that the surgical device 112 is present in the scanning chamber 124. Any further arcing from the single sweeping contact 126 is then processed by the PCB 136 as evidence of an insulation defect.

Figure 5:
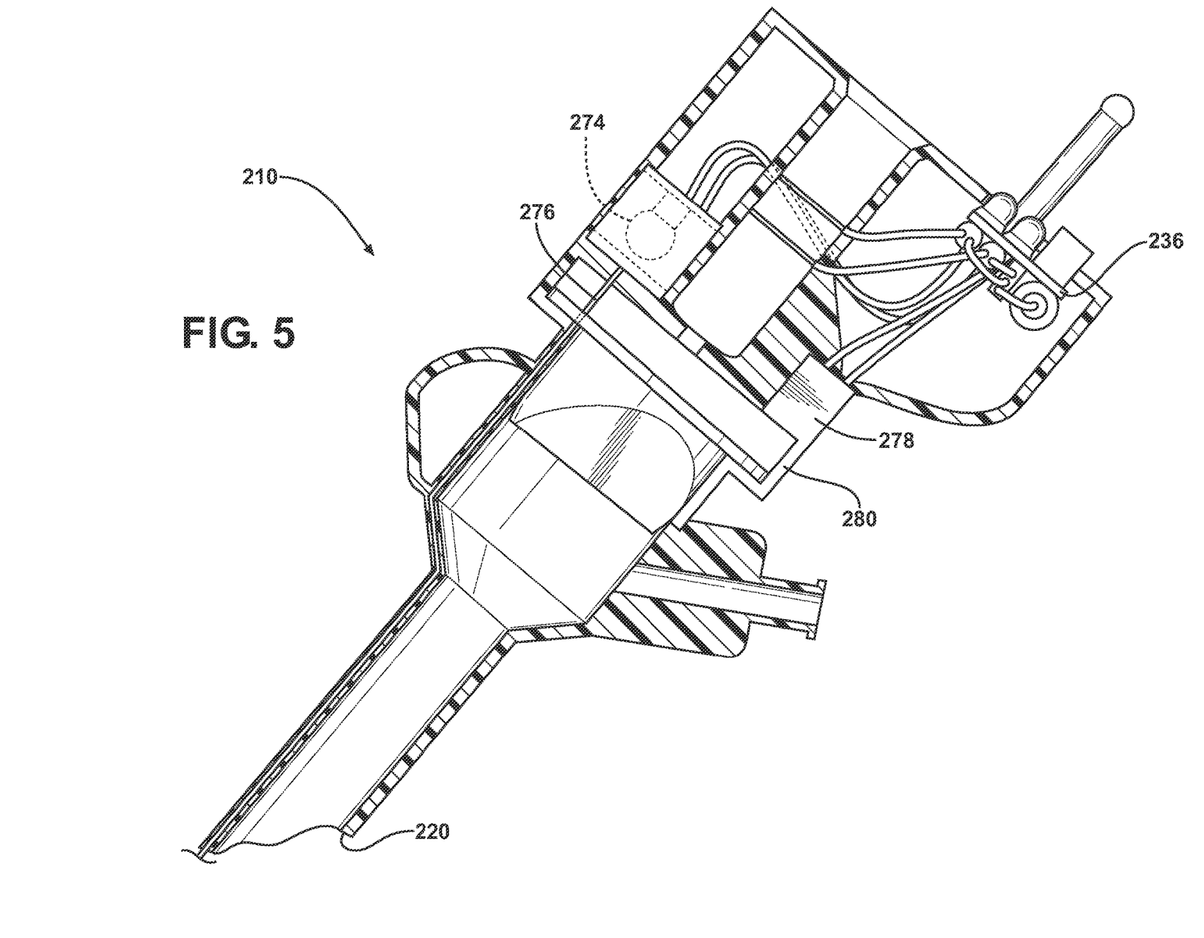
FIG. 5 is a partial view of another alternative embodiment of a scanning cannula in accordance with the invention.

In yet another embodiment illustrated in FIG. 5, the scanning cannula 210 may optionally include a light source 274 such as a bulb or similar that emits light which is then transmitted via optical fibers 276 or other transmission means such as a built-in light conduit or similar. Light from the light source 274 glows through the distal tubular exit end 220 of the scanning cannula 210, to aid in illumination when needed and traceability during the penetration stage. The scanning cannula 210 may also include dynamic pressure monitoring of insufflation pressure. A pressure sensor 278 may read cannula/insufflation pressure via conduit 280. The scanning cannula may even control an insuflator (not shown) remotely. The light source 274 and pressure sensor 278 may each be electrically connected to the PCB 236.

Figure 6:
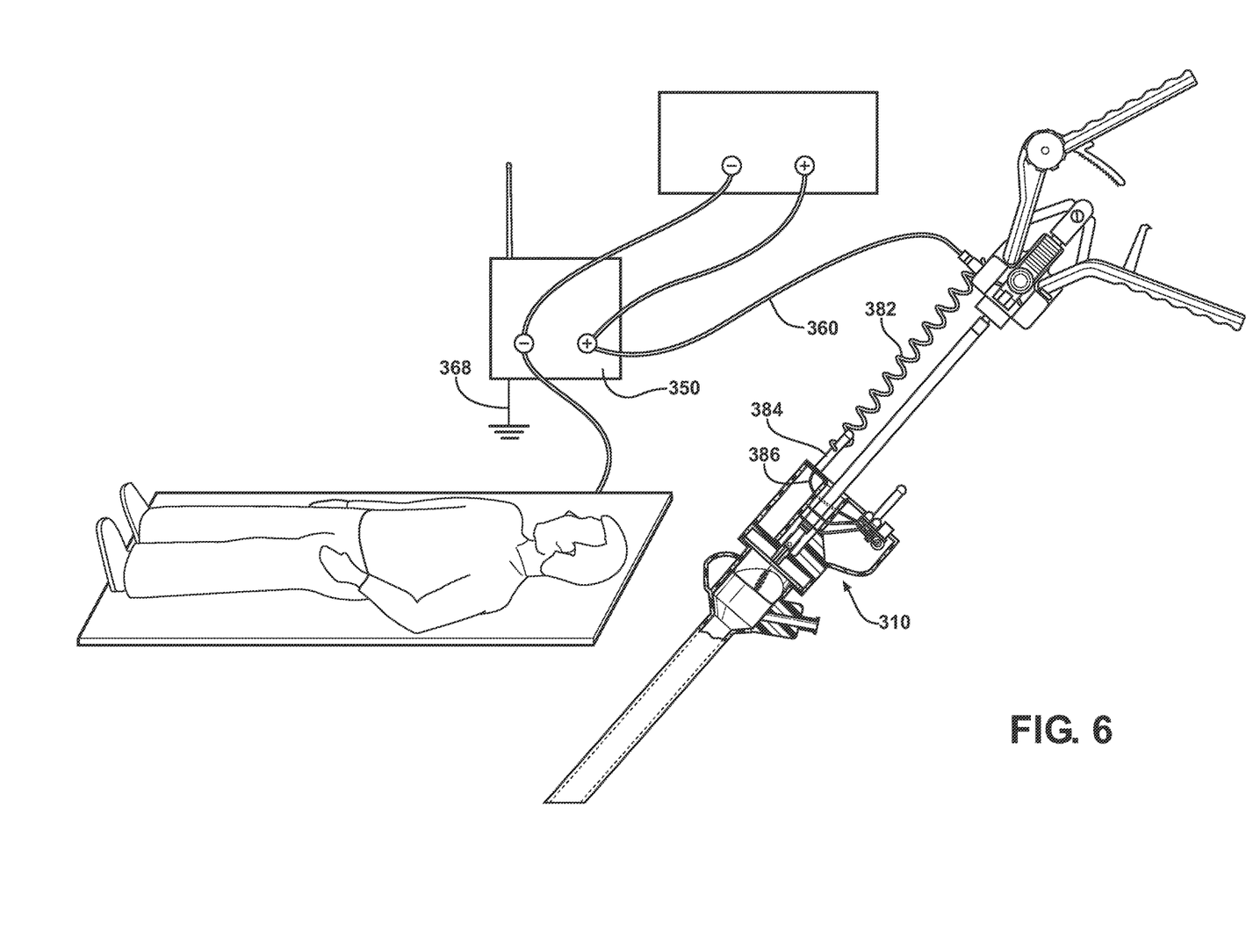
FIG. 6 is an environmental view of yet another alternative embodiment of a scanning cannula in accordance with the invention.

In an alternative embodiment, the scanning cannula 310 may be arranged in wired form, i.e., using a powered, multi-channel cable from the switchbox 350 into the scanning cannula 310 and eliminating the battery in the PCB. An example is illustrated in FIG. 6, in which powered cable 382, branched from cable 360, is connected with the scanning cannula 310 circuitry via power plug 384 and wires 386. Wireless communication is therefore not required as the physical connection (i.e., cable) with the switchbox 350 may be used to convey information such as test mode beginning, test mode end, and scanning results. A decision to cutoff power to the electrosurgical generator 352 may be made in the switchbox 350 or the generator 352, if equipped properly. Optionally, another ground reference may be achieved by having the switchbox 350 include an attached ground wire 368, thus avoiding the use of patient capacitance as the ground reference.

Any combination of the above described embodiments is within the scope of the invention.

Although the present invention has been described in relation to endoscopic applications, the principles and the basic design of the scanning chamber 24 may apply to many industrial and general fields, where simple scanning of dielectric barrier defects is required. Further, even though a wireless embodiment is described herein, the same scanning principles may apply to a wired scanning cannula, i.e., a similar device that is wired to a switchbox with a multi-channel cable, branched and connected to the scanning cannula 10 at scanning chamber 24.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A scanning cannula configured to be activated during a surgery for scanning an electrosurgical instrument for electrical defects while the scanning cannula is disposed in a body of a patient, said scanning cannula comprising:
   a receiving end and an opposite exit end;
   a scanning chamber disposed at said receiving end;
   an elongated sleeve configured to be disposed in the body of a patient and disposed at said opposite exit end, having an extended passageway axially spaced from said scanning chamber in communication with said scanning chamber;
   said scanning chamber extending from said receiving end proximal to said elongated sleeve;
   a pair of sweeping contacts configured to be spacedly disposed from each other in and disposed only in said scanning chamber at said receiving end of said scanning cannula, each of said pair of sweeping contacts being a disk-shaped ring including a plurality of fingers extending towards a hollow center of said disk-shaped ring;
   a circuit configured to be integral with said scanning chamber, said pair of sweeping contacts being electrically connected to said circuit; and
   a communication device configured to be connected to said circuit to transmit signals from said circuit to a switchbox of said electrosurgical instrument;
   wherein when said electrosurgical instrument is inserted into said receiving end of said elongated sleeve and passes through said pair of sweeping contacts during said surgery, any electrical defect of the electrosurgical instrument detected by said pair of sweeping contacts is relayed as an error signal to said circuit, which communicates the error signal to the switchbox.

2. The scanning cannula of claim 1, wherein said communication device includes an antenna configured to wirelessly transmit signals to the switchbox.

3. The scanning cannula of claim 1, wherein said communication device includes a cable that electrically transmits signals to the switchbox.

4. The scanning cannula of claim 1, including a photo cell disposed in said passageway downstream of said at least one sweeping contact, said photo cell configured to be electrically connected to said circuit, wherein said photo cell is configured to detect the presence of an electrosurgical instrument in said passageway.

5. The scanning cannula of claim 1, wherein said circuit includes a battery that is configured to power said scanning cannula.

6. The scanning cannula of claim 1, wherein said circuit includes a capacitor configured to be electrically connected to each of at least one of said pair of sweeping contacts.

7. The scanning cannula of claim 1, wherein said circuit includes two or more LEDs that are configured to display status information.

8. The scanning cannula of claim 1, including a light source configured to be in communication with an optical fiber disposed along a length of said elongated sleeve to illuminate said elongated sleeve.

9. The scanning cannula of claim 1, including a pressure sensor configured to be electrically connected to said circuit, and a conduit in fluid communication with said pressure sensor for dynamic monitoring of insufflation pressure.

10. An electrosurgical system for scanning an electrosurgical instrument for electrical defects, said system comprising:
    a scanning cannula including:
    a receiving end and an opposite exit end;
    a scanning chamber disposed at said receiving end:
    an elongated sleeve configured to be disposed in the body of a patient disposed at said opposite exit end having an extended passageway axially spaced from said scanning chamber;
    a wall disposed between said scanning chamber and said elongated sleeve having a passageway in said wall;
    said scanning chamber extending from said receiving end to said wall;

a pair of contacts configured to be spacedly fixed in position relative to said scanning chamber, and disposed only within said scanning chamber;

a circuit configured to be mounted in and integral with said scanning chamber, said pair of contacts configured to be electrically connected to said circuit; and a communication device configured to be connected to said circuit to transmit signals from said circuit;

a switchbox configured to be in communication with said scanning cannula;

an electrosurgical generator configured to be electrically connected to said switchbox;

said electrosurgical instrument electrically connected to said switchbox;

wherein said electrosurgical instrument is configured to be inserted into said receiving end of said scanning cannula and passes through said pair of contacts, and any electrical defect of said electrosurgical instrument detected by said pair of contacts is relayed as an error signal to said circuit, which communicates the error signal to said switchbox.

11. The electrosurgical system of claim 10, wherein said communication device includes an antenna, and said circuit is configured to wirelessly communicate with said switchbox via said antenna.

12. The electrosurgical system of claim 10, wherein said communication device includes a cable that is configured to be electrically connected to said circuit and said switchbox, and said circuit configured to communicate with said switchbox through said cable.

13. The electrosurgical system of claim 10, wherein said switchbox is configured to receive said error signal from said scanning cannula, and said switchbox is configured to display a warning signal.

14. The electrosurgical system of claim 10, wherein said switchbox is configured to receive said error signal from said scanning cannula, and said switchbox is configured to cut power to said electrosurgical device.

15. A scanning cannula comprising:
an elongated tubular element comprising the outer surface of said scanning cannula as configured to be inserted into a body of a patient, having a receiving end, an opposite exit end, and a passageway extending from said receiving end to said opposite exit end and configured to receive an electrosurgical instrument;
said receiving end comprising a scanning chamber,
at least one sweeping contact disposed integrally within and only within said scanning chamber and configured to be activated during a surgery on the patient;
at least one controller;
wherein said electrosurgical instrument is configured to be inserted into said receiving end of said elongated tubular element while any portion of said elongated tubular element is disposed in the body during the surgery and pass through said at least one sweeping contact in said scanning chamber, and any electrical defect of said electrosurgical instrument detected by said at least one sweeping contact is relayed as an error signal to communicate to a switchbox during the surgery.

16. An electrosurgical system for scanning an electrosurgical instrument for electrical defects, said electrosurgical system comprising:
a scanning cannula including:
a cannula having a receiving end, an opposite exit end, and a passageway extending from said receiving end to said exit end with said opposite exit end configured to be disposed in a body of a patient;
a scanning chamber disposed at said receiving end of said cannula;
at least one sweeping contact configured to be disposed only in said scanning chamber and configured to be activated when said cannula is disposed in the body of the patient;
a circuit mounted in said scanning chamber, said at least one sweeping contact being configured to be electrically connected to said circuit while said scanning cannula is disposed in the body of the patient; and
a communication device configured to be connected to said circuit to transmit signals from said circuit during a surgery on the patient;
a controller configured to be in communication with said scanning cannula;
an electrosurgical generator configured to be electrically connected to said controller;
an electrosurgical instrument configured to be electrically connected to said controller;
wherein when said electrosurgical instrument is inserted into said receiving end of said cannula and passes through said at least one sweeping contact during surgery, any electrical defect of said electrosurgical instrument detected by said at least one sweeping contact is relayed as an error signal to a switchbox.

17. A scanning cannula for scanning an electrosurgical instrument for electrical defects, said scanning cannula comprising:
an elongated sleeve—having a receiving end, an opposite exit end and a passageway extending from said receiving end to said exit end—, at least a portion of said elongated sleeve is configured to be disposed in the patient during a surgery and in contact with a portion of the body of the patient during the surgery;
a scanning chamber disposed at said receiving end of said elongated sleeve;
a separate second chamber the exterior surface of which is configured to be disposed in the body of the patient and disposed at said opposite exit end having an extended passageway axially spaced from and in communication with said scanning chamber;
said scanning chamber extending from said receiving end proximal to said second chamber;
a pair of sweeping contacts configured to be spacedly disposed from each other and only at the scanning chamber, each of said pair of sweeping contacts being a disk-shaped ring including a ring and a plurality of fingers extending towards a hollow center of said ring:
a circuit integral with said scanning chamber, each of said pair of sweeping contacts configured to be electrically connected to said circuit; and
a communication device configured to be connected to said circuit to transmit signals from said circuit to a switchbox of a surgical instrument;
wherein said pair of sweeping contacts, said circuit, and said communication device are configured to be activated during the surgery; and
an electrosurgical instrument is configured to be inserted into said receiving end of said elongated sleeve and pass through said pair of sweeping contacts, any electrical defect of said electrosurgical instrument detected by said pair of sweeping contacts is relayed as an error signal to said circuit to the switchbox at any time after the scanning cannula is in place in the patient.

18. A scanning cannula comprising: an elongated tubular element comprising a cannula configured to be inserted into a body of a patient, having a receiving end, an opposite exit end, and a passageway extending from said receiving end to said exit end configured to receive an electrosurgical instrument; a scanning chamber disposed at said receiving end; an elongated sleeve configured to be disposed in the body of a patient disposed at said opposite exit end having a chamber axially spaced from said scanning chamber in communication with said scanning chamber; said scanning chamber extending from said receiving end proximal to said chamber of said elongated sleeve; at least one sweeping contact disposed integrally and not axially movable relative to the cannula within said scanning chamber and configured to be activated during a surgery on the patient; at least one controller; wherein said electrosurgical instrument inserted into said receiving end of said elongated tubular element while any portion of said elongated tubular element is disposed in the body during the surgery can pass through at least one sweeping contact, and any electrical defect of said electrosurgical instrument detected by said at least one sweeping contact is relayed as an error signal to communicate to a switchbox during the surgery, and wherein said electrosurgical instrument exits the cannula at said exit end to release the electrosurgical instrument to perform activity on the patient body.

19. A scanning cannula device comprising:
a cannula configured to be inserted into a body of a patient having a receiving end, an opposite exit end, and a passageway extending from said receiving end to said exit end configured with an internal cylindrical surface divided into at least two chambers, a scanning chamber and a second chamber;
at least one sweeping contact disposed only within said scanning chamber and associated with the elongated tubular element, and configured to be activated during a surgery on the patient;
at least one controller;
wherein an electrosurgical instrument inserted into said at least one sweeping contact enters said scanning chamber, and any electrical defect of said electrosurgical instrument detected by said at least one sweeping contact is relayed as an error signal to communicate to a switchbox during the surgery.

20. A scanning cannula assembly comprising:
a cannula configured to be inserted into a body of a patient having a receiving end, an opposite exit end, and a passageway extending from said receiving end to said exit end configured as a space divided into at least two separate chambers, a scanning chamber and a second chamber, the exterior surface of which the second chamber is configured to be inserted into the body of the patient, and which the at least two separate chambers are configured to receive an electrosurgical instrument;
at least one sweeping contact disposed only in said scanning chamber and not movable relative to the cannula during use, is configured to be activated during a surgery on the patient;
at least one controller;
wherein when said electrosurgical instrument is inserted into said receiving end of said cannula while a portion of said cannula is disposed in the body during the surgery, said electrosurgical instrument passes through said at least one sweeping contact, and any electrical defect of said electrosurgical instrument detected by said at least one sweeping contact is relayed as an error signal to communicate to a switchbox during the surgery, and
wherein said electrosurgical instrument is configured to exit the cannula at said exit end to release the electrosurgical instrument to perform activity on the body of the patient.

* * * * *